(12) United States Patent
Masuda et al.

(10) Patent No.: US 8,287,294 B2
(45) Date of Patent: Oct. 16, 2012

(54) CONNECTOR

(75) Inventors: Koichi Masuda, Nagoya (JP); Hirohito Kiyota, Kiyosu (JP); Nobukazu Ikoma, Nagoya (JP)

(73) Assignee: NGK Insulators, Ltd., Nagoya (JP)

( * ) Notice: Subject to any disclaimer, the term of this patent is extended or adjusted under 35 U.S.C. 154(b) by 0 days.

(21) Appl. No.: 13/194,088

(22) Filed: Jul. 29, 2011

(65) Prior Publication Data

US 2011/0281472 A1 Nov. 17, 2011

Related U.S. Application Data

(63) Continuation of application No. PCT/JP2010/072612, filed on Dec. 16, 2010.

(30) Foreign Application Priority Data

Dec. 25, 2009 (JP) ................................ 2009-295652

(51) Int. Cl.
*H01R 13/15* (2006.01)

(52) U.S. Cl. ..................................... 439/260

(58) Field of Classification Search .................. 439/260, 439/33, 660, 885; 73/31.05, 23.2; 204/424, 204/427

See application file for complete search history.

(56) References Cited

U.S. PATENT DOCUMENTS

| | | | |
|---|---|---|---|
| 4,983,271 A | 1/1991 | Kato et al. | |
| 5,246,562 A | 9/1993 | Weyl et al. | |
| 5,711,863 A * | 1/1998 | Henkelmann et al. | 204/428 |
| 5,922,938 A * | 7/1999 | Hafele | 73/23.32 |
| 6,082,175 A * | 7/2000 | Yoshikawa et al. | 73/23.31 |
| 6,231,348 B1 * | 5/2001 | Mayer et al. | 439/33 |
| 6,477,887 B1 * | 11/2002 | Ozawa et al. | 73/31.05 |
| 6,613,206 B1 * | 9/2003 | Weyl et al. | 204/424 |
| 6,615,641 B2 * | 9/2003 | Kojima | 73/23.31 |
| 6,672,136 B2 * | 1/2004 | Kojima | 73/31.05 |
| 6,688,157 B2 * | 2/2004 | Yamada et al. | 73/23.2 |
| 6,812,710 B2 * | 11/2004 | Weyl et al. | 324/464 |
| 6,866,517 B2 * | 3/2005 | Kimata et al. | 439/33 |
| 7,302,828 B2 * | 12/2007 | Uchikawa et al. | 73/23.31 |
| 7,340,942 B2 * | 3/2008 | Matsuo et al. | 73/31.05 |
| 7,399,925 B2 * | 7/2008 | Yamauchi | 174/74 R |
| 7,404,883 B2 * | 7/2008 | Hahn et al. | 204/428 |
| 7,424,819 B2 * | 9/2008 | Fujita et al. | 73/31.05 |
| 7,461,538 B2 * | 12/2008 | Matsuo et al. | 73/23.31 |
| 7,563,118 B1 * | 7/2009 | McCauley et al. | 439/260 |

(Continued)

FOREIGN PATENT DOCUMENTS

JP 02-146365 U 12/1990

(Continued)

*Primary Examiner* — Alexander Gilman
(74) *Attorney, Agent, or Firm* — Burr & Brown (57) ABSTRACT

Each of contact fittings is obtained by bending a die-cut member having a metal plate portion of substantially rectangular shape and a metal piece connecting to a long side of the metal plate portion. The metal piece is folded to be accommodated within a region directly above a surface of the metal plate portion opposite a surface in contact with a front-surface electrode or a back-surface electrode. Then, the metal piece is bent along the length of the metal plate portion to form a hook to be retained by a first housing or a second housing. Therefore, as compared to a structure in which hooks are orthogonal to the length of metal plate portions and bend outward from contact fittings, the arrangement width of the contact fittings arranged in a direction substantially orthogonal to the length of the contact fittings can be reduced.

6 Claims, 7 Drawing Sheets

U.S. PATENT DOCUMENTS

| | | | |
|---|---|---|---|
| 7,569,792 B2 * | 8/2009 | Yamada et al. | 219/121.63 |
| 7,589,280 B2 * | 9/2009 | Nelson | 174/84 C |
| 8,047,051 B2 * | 11/2011 | Mccauley et al. | 73/23.31 |
| 2001/0025522 A1 | 10/2001 | Kojima | |
| 2004/0074284 A1 * | 4/2004 | Day et al. | 73/23.31 |

FOREIGN PATENT DOCUMENTS

| | | |
|---|---|---|
| JP | 3061227 U | 6/1999 |
| JP | 11-248671 A1 | 9/1999 |
| JP | 2001-343356 A1 | 12/2001 |
| JP | 2002-340847 A1 | 11/2002 |

* cited by examiner

12;# CONNECTOR

TECHNICAL FIELD

The present invention relates to connectors.

BACKGROUND ART

Figure 10:
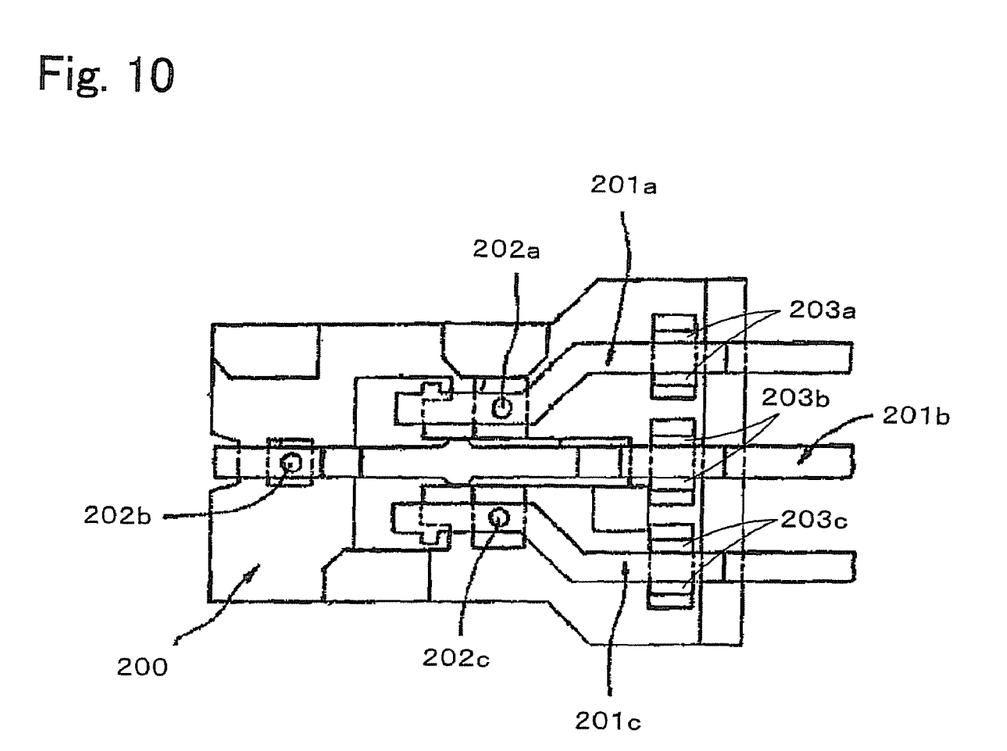
FIG. 10 illustrates contact fittings 201a to 201c and a housing 200 of related art.

Conventionally, a connector has been known which is electrically connected to a plurality of front-surface electrodes arranged side by side on a front surface of a planar sensor element and to a plurality of back-surface electrodes arranged side by side on a back surface of the sensor element. For example, Patent Document 1 describes a gas sensor that includes a planar sensor element configured to detect gas, conductors such as lead wires, and a connector configured to connect the sensor element and the conductors. The connector of the gas sensor includes contact fittings that are electrically connected to the sensor element, and housings that holds the contact fittings. The sensor element is clamped by two housings. FIG. 10 illustrates contact fittings 201a to 201c and a housing 200 of such related art. As illustrated, the contact fittings 201a to 201c are provided with protrusions 202a to 202c, respectively, at which the contact fittings 201a to 201c come into contact with and are electrically connected to front-surface electrodes and back-surface electrodes of the sensor element. The contact fittings 201a to 201c are also provided with hooks 203a to 203c, respectively, which are orthogonal to the length of the contact fittings 201a to 201c and bend outward from the contact fittings 201a to 201c. The contact fittings 201a to 201c are arranged in a direction orthogonal to the length of the contact fittings 201a to 201c and secured to the housing 200 by the hooks 203a to 203c.

Patent Document 1: U.S. Pat. No. 5,246,562 (FIG. 7 and FIG. 8)

DISCLOSURE OF INVENTION

However, if there are such hooks that are orthogonal to the length of contact fittings and bend outward from the contact fittings, the contact fittings need to be widely spaced orthogonally to the length thereof. This increases the size of the housing and hence the size of the connector.

The present invention has been made to solve the problem described above. A primary object of the present invention is to provide a connector of reduced size.

To achieve the primary object described above, a connector of the present invention adopts the following means.

A connector of the present invention electrically connected to a plurality of front-surface electrodes arranged side by side on a front surface of a planar sensor element and to a plurality of back-surface electrodes arranged side by side on a back surface of the sensor element, the connector comprising: a first housing configured to hold a plurality of long narrow contact fittings arranged at respective positions opposite the plurality of front-surface electrodes of the sensor element in a direction substantially orthogonal to the length of the contact fittings; and a second housing configured to hold a plurality of long narrow contact fittings arranged at respective positions opposite the plurality of back-surface electrodes of the sensor element in a direction substantially orthogonal to the length of the contact fittings, wherein each of the contact fittings is obtained by bending a die-cut member having a metal plate portion of substantially rectangular shape and a metal piece connecting to a long side of the metal plate portion; the metal plate portion has a conducting portion that can be in contact with the front-surface electrode or the back-surface electrode; and the metal piece is folded to be accommodated within a region directly above a surface of the metal plate portion opposite a surface in contact with the front-surface electrode or the back-surface electrode, and bent along the length of the metal plate portion to form a hook to be retained by the first housing or the second housing.

In the connector described above, the first housing holds the plurality of long narrow contact fittings arranged at respective positions opposite the plurality of front-surface electrodes of the planar sensor element in the direction substantially orthogonal to the length of the contact fittings, and the second housing holds the plurality of long narrow contact fittings arranged at respective positions opposite the plurality of back-surface electrodes of the planar sensor element in the direction substantially orthogonal to the length of the contact fittings. Each of the contact fittings is obtained by bending a die-cut member having a metal plate portion of substantially rectangular shape and a metal piece connecting to a long side of the metal plate portion. The metal piece is folded to be accommodated within a region directly above a surface of the metal plate portion opposite a surface in contact with the front-surface electrode or the back-surface electrode. Then, the metal piece is bent along the length of the metal plate portion to form a hook to be retained by the first housing or the second housing. Therefore, as compared to a structure in which hooks are orthogonal to the length of metal plate portions and bend outward from contact fittings, the arrangement width of the contact fittings arranged in the direction substantially orthogonal to the length of the contact fittings can be reduced, so that the size of the first housing and the second housing can be reduced. This means that it is possible to reduce the size of the connector.

The connector according to the present invention may further include regulating members configured to regulate a distance between the first housing and the second housing; and a housing securing member configured to apply pressure to bring the first housing and the second housing closer to each other, with the front-surface electrodes of the sensor element facing the respective conducting portions of the contact fittings on the first housing and the back-surface electrodes of the sensor element facing the respective conducting portions of the contact fittings on the second housing, allow the regulating members to fix the distance between the first housing and the second housing, and clamp and secure the sensor element with pressing force generated by elastic deformation of the conducting portions of the contact fittings on the first housing and the conducting portions of the contact fittings on the second housing. Thus, since the conducting portions clamp the sensor element with pressing force generated by elastic deformation, the conducting portions are less likely to separate from the sensor element. This makes it possible to reliably maintain the electrical contact between the conducting portions and the front-surface electrodes and between the conducting portions and the back-surface electrodes, and to reliably clamp the sensor element. Additionally, since the distance between the first housing and the second housing is fixed by the regulating members, even if excessive pressure is externally applied, the conducting portions are not affected by the pressure and can be prevented from being plastically deformed. It is thus possible to maintain the electrical contact and the clamping of the sensor element for a long period of time, and to ensure longer life of the connector. If a sensor including this connector is used in a vibrating environment, such as in a vehicle, where the connector is often subjected to such excessive pressure, it is particularly useful to apply the present invention. In this case, it is preferable that a spring constant of the conducting portion of each of the contact fittings be in the range of 500 N/mm to 4000 N/mm.

BRIEF DESCRIPTION OF DRAWINGS

FIG. 6 illustrates a positional relationship between contact fittings 71 and a sensor element 20 as viewed from a first housing 51a.

BEST MODES FOR CARRYING OUT THE INVENTION

Embodiments of the present invention will now be described with reference to the drawings.

Figure 1:
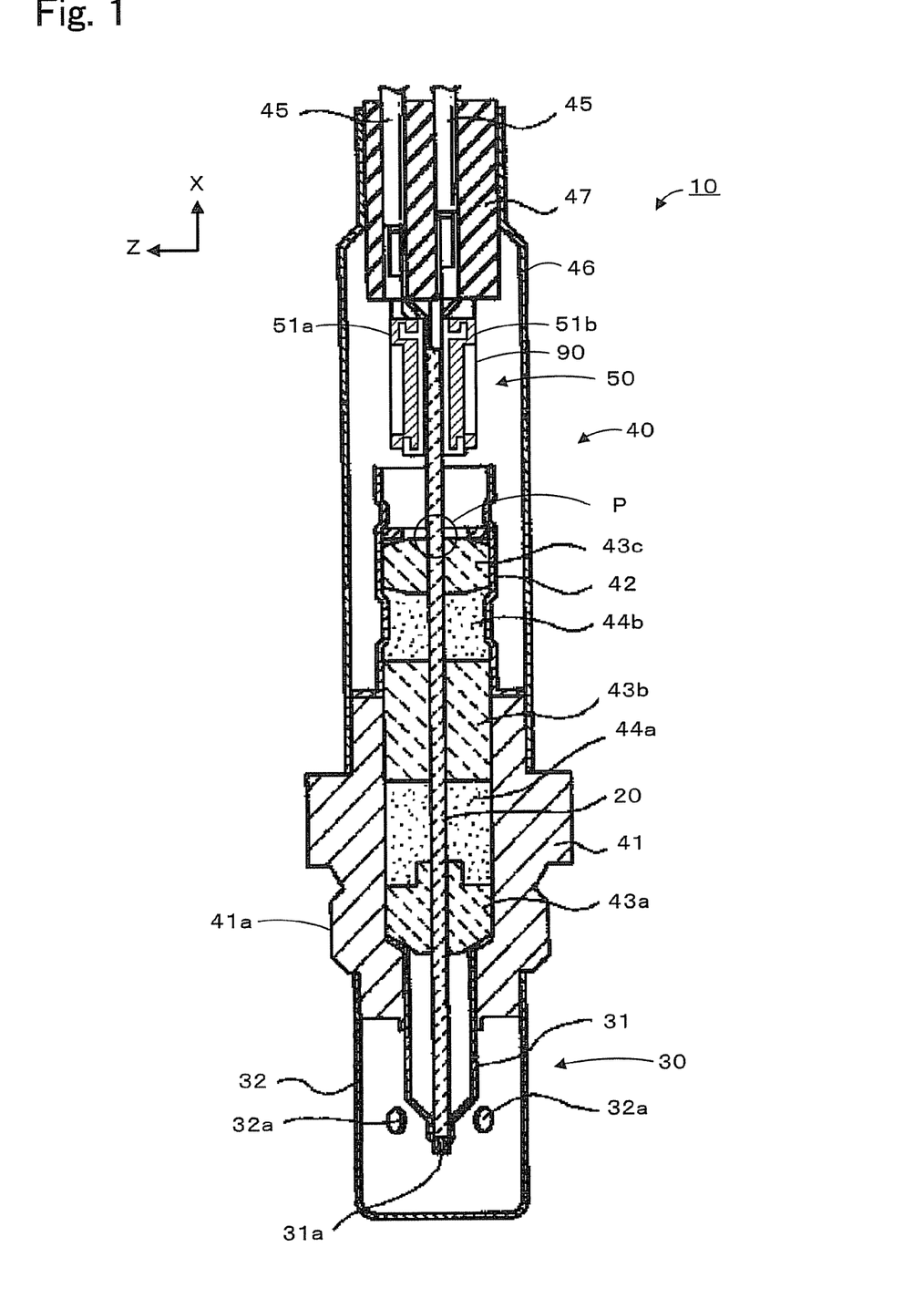
FIG. 1 is a longitudinal cross-sectional view of a gas sensor 10 according to the present embodiment.
Figure 2:
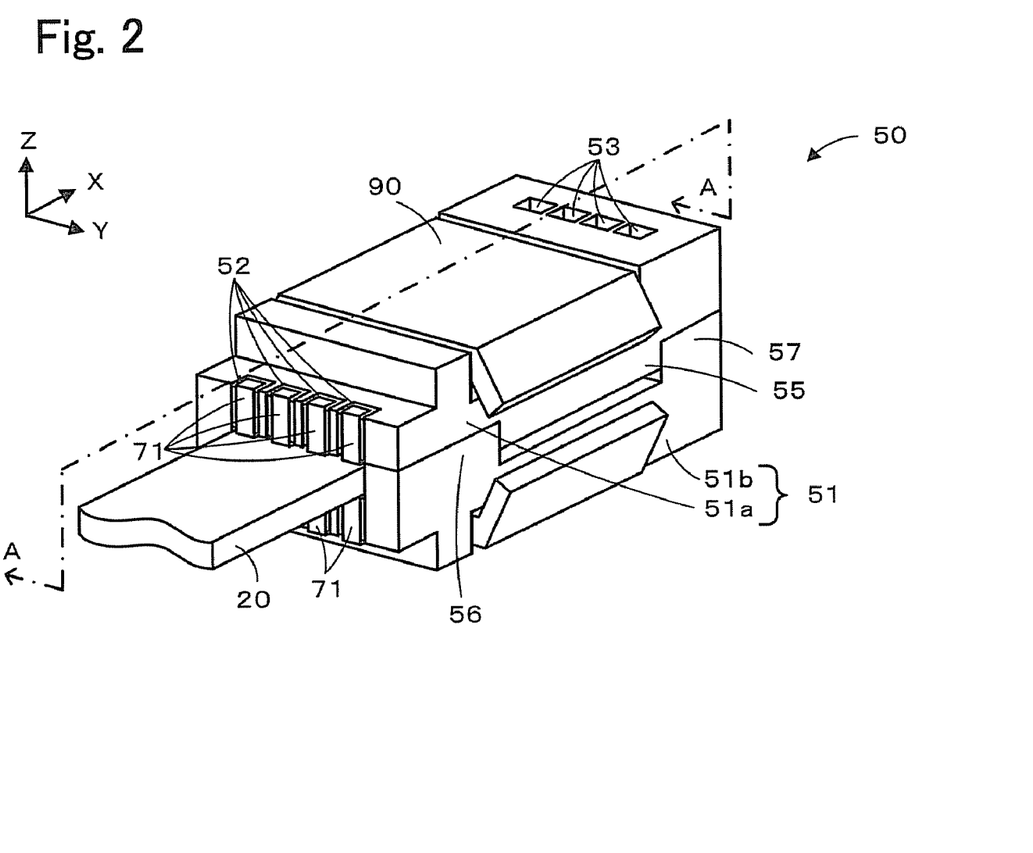
FIG. 2 is a perspective view of a connector 50.
Figure 3:
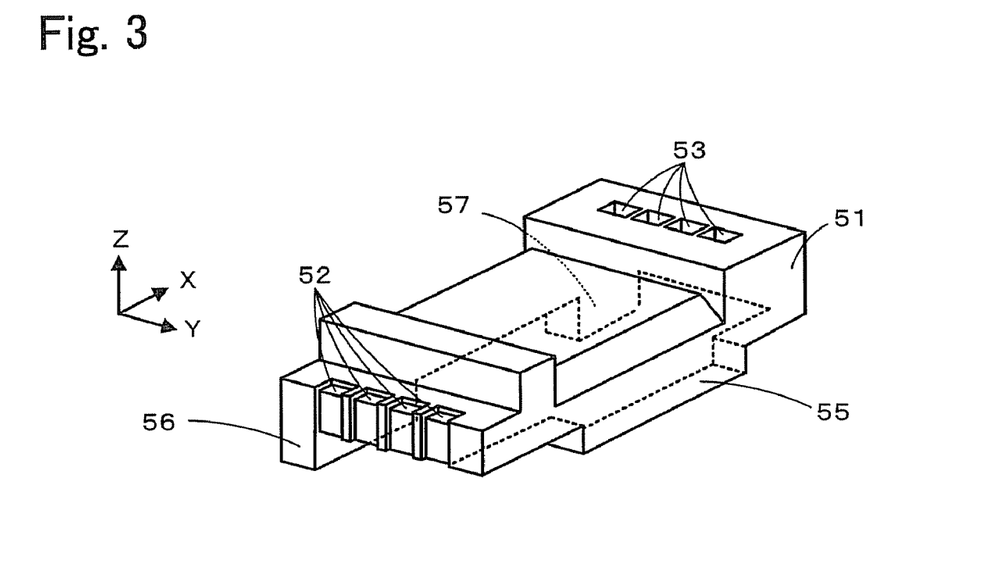
FIG. 3 is an exploded perspective view illustrating a housing 51 of the connector 50.
Figure 4:
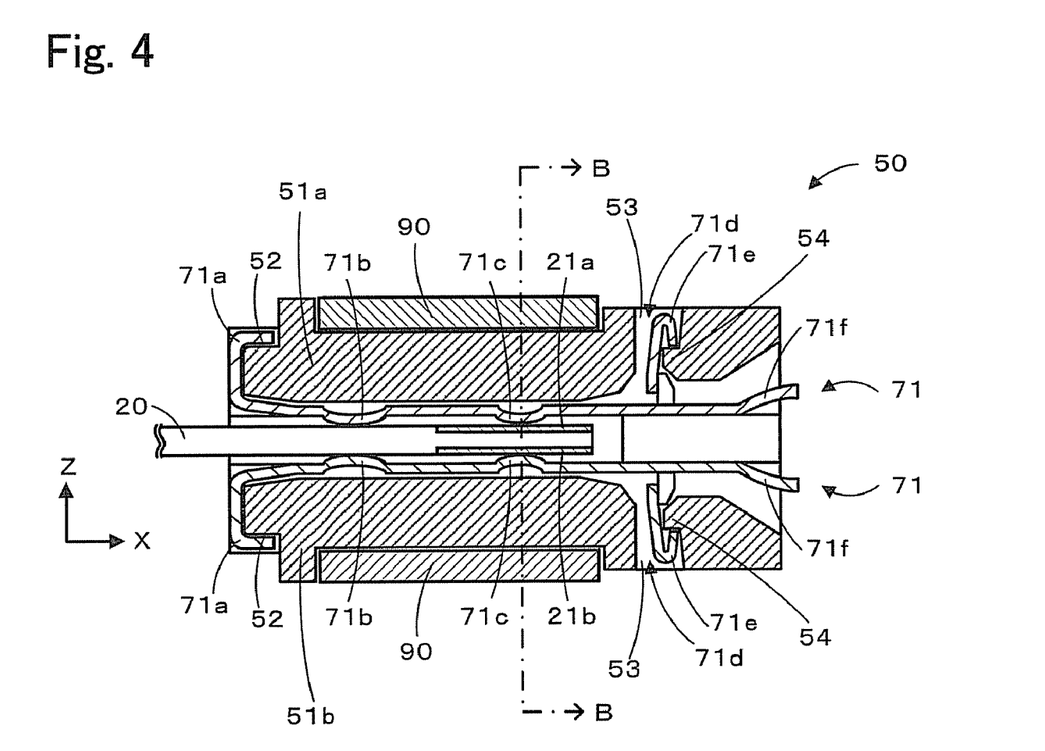
FIG. 4 is a cross-sectional view taken along line A-A of FIG. 2.
Figure 5:
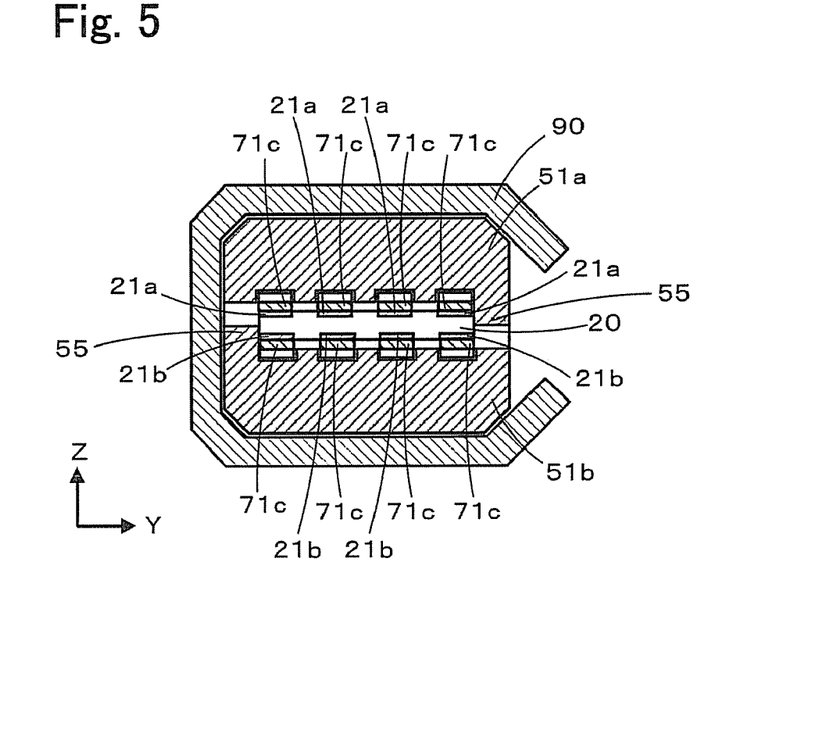
FIG. 5 is a cross-sectional view taken along line B-B of FIG. 4.
Figure 6:
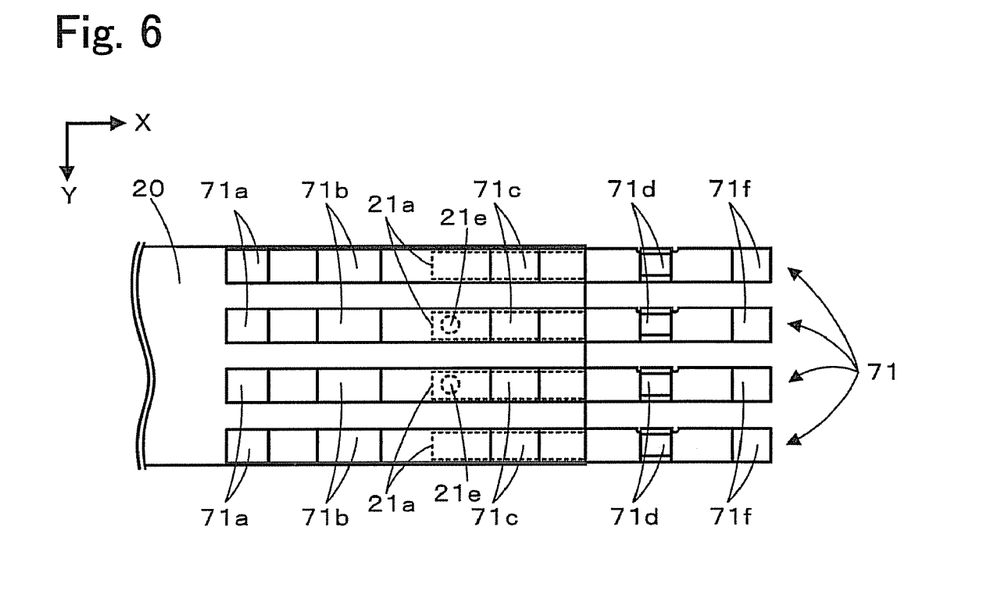

FIG. 1 is a longitudinal cross-sectional view of a gas sensor 10 according to an embodiment of the present invention. FIG. 2 is a perspective view of a connector 50. FIG. 3 is an exploded perspective view illustrating a housing 51 of the connector 50. FIG. 4 is a cross-sectional view taken along line A-A of FIG. 2. FIG. 5 is a cross-sectional view taken along line B-B of FIG. 4. FIG. 6 illustrates a positional relationship between contact fittings 71 and a sensor element 20 as viewed from a first housing 51a.

As illustrated in FIG. 1, the gas sensor 10 includes the sensor element 20 that measures a predetermined gas component in gas under measurement, a protective cover 30 that protects an end portion of the sensor element 20, and a sensor assembly 40 that includes the connector 50 electrically connected to the sensor element 20. For example, the gas sensor 10 is attached to an exhaust gas pipe of a vehicle and used to measure gas components, such as NOx and $O_2$, contained in exhaust gas, which is gas under measurement.

The sensor element 20 is a long narrow planar element. The sensor element 20 is formed by stacking, for example, six ceramic substrates composed of oxygen-ion conductive solid electrolyte layers, such as zirconia ($ZrO_2$) layers. An end portion of the sensor element 20 adjacent to the protective cover 30 is referred to as a tip end, and the other end portion of the sensor element 20 adjacent to the connector 50 is referred to as a base end. As illustrated in FIG. 5, four front-surface electrodes 21a and four back-surface electrodes 21b are formed on front and back surfaces of the base end of the sensor element 20. The front-surface electrodes 21a and the back-surface electrodes 21b are collectively referred to as electrodes 21. The electrodes 21 are for applying a voltage to the sensor element 20, and for deriving electromotive force or current which is generated in accordance with the concentration of a gas component detected by the sensor element 20. The electrodes 21 are electrically connected, through electric paths inside the sensor element 20, to electrodes (not shown) within the tip end of the sensor element 20. The positions of the front-surface electrodes 21a and the back-surface electrodes 21b will be described later on.

As illustrated in FIG. 1, the protective cover 30 is disposed around the tip end of the sensor element 20. The protective cover 30 includes an inner protective cover 31 that covers the tip end of the sensor element 20, and an outer protective cover 32 that covers the inner protective cover 31. The inner protective cover 31 has a cylindrical shape and is provided with an inner protective cover hole 31a, at the tip end of the sensor element 20, for introducing gas under measurement. The outer protective cover 32 has a cylindrical shape with a bottom and is provided with outer protective cover holes 32a, in the periphery thereof, for introducing gas under measurement. The inner protective cover 31 and the outer protective cover 32 are made of metal, such as stainless steel.

The sensor assembly 40 includes a main fitting 41 made of metal, an inner cylinder 42 and an outer cylinder 46 having a cylindrical shape and secured by welding to the main fitting 41, and the connector 50 connected to the base end of the sensor element 20. The main fitting 41 can be attached, for example, to an exhaust gas pipe of a vehicle with an external thread 41a. The inner cylinder 42 contains a plurality of ceramic supporters 43a to 43c, and ceramic powder 44a and 44b, such as talc powder, with which a space between the ceramic supporters 43a and 43b and a space between the ceramic supporters 43b and 43c are filled. The inner cylinder 42, the sensor element 20, and the connector 50 are surrounded by the outer cylinder 46. Lead wires 45 connected to the connector 50 are pulled out of the outer cylinder 46. The lead wires 45 are electrically connected through the connector 50 to the electrodes 21 of the sensor element 20. Gaps between the outer cylinder 46 and the lead wires 45 are sealed with a rubber stopper 47. The sensor element 20 passes through the ceramic supporters 43a to 43c and the ceramic powder 44a and 44b, and is secured mainly by the main fitting 41 and the ceramic powder 44a and 44b. Therefore, for example, if the gas sensor 10 is installed in a vibrating environment such as in a vehicle, a part of the sensor element 20 on one side of an upper end portion P adjacent to the connector 50, the connector 50, and the lead wires 45 vibrate with respect to the upper end portion P of the ceramic supporter 43c. On the other hand, a part of the sensor element 20 on the other side of the upper end portion P adjacent to the protective cover 30 is less affected by vibration, as it is covered with the main fitting 41 and the ceramic powder 44a and 44b.

The connector 50 will now be described in detail. As illustrated, the connector 50 includes the first housing 51a and a second housing 51b made of ceramic such as sintered alumina, the contact fittings 71 held by the first housing 51a or the second housing 51b and in contact with the respective electrodes 21 of the sensor element 20, and a metal clamp 90 configured to clamp and secure the first housing 51a and the second housing 51b.

The first housing 51a and the second housing 51b each are configured to hold four contact fittings 71 arranged in a direction (Y direction) orthogonal to the length (X direction) of the contact fittings 71. The same components in the first housing 51a and the second housing 51b, which are of the same shape, are denoted by the same reference numerals. The first housing 51a and the second housing 51b are collectively referred to as the housings 51. Each housing 51 includes four retaining grooves 52 for retaining the contact fittings 71, four insertion holes 53 for insertion of the contact fittings 71, and retainers 54 formed in the respective insertion holes 53 and retaining the contact fittings 71. Each housing 51 has a protrusion 55 in one side thereof and regulating members 56 and 57 in the other side thereof in the Y direction, with the sensor element 20 interposed therebetween (see FIG. 2 and FIG. 3). The regulating members 56 and 57 regulate the distance between the first housing 51a and the second housing 51b in the Z direction. The protrusion 55 is configured to fit in an indentation between the regulating member 56 and the regulating member 57 of the opposite housing 51 and thus, the relative position of the first housing 51a and the second housing 51b in the X direction can be fixed.

The contact fittings 71 are held by the housing 51 at positions where they face the respective electrodes 21 of the sensor element 20. Each of the contact fittings 71 includes a tip portion 71a having a curved shape and retained by the retaining groove 52, a supporting portion 71b bending toward the sensor element 20, a conducting portion 71c bending toward the sensor element 20 to come into contact with the electrode 21, an upright portion 71d in the insertion hole 53, and a connecting portion 71f pulled out of the connector 50 and electrically connected to the lead wire 45. The conducting portions 71c of the contact fittings 71 held by the first housing 51a face and are in contact with the respective front-surface electrodes 21a of the sensor element 20, while the conducting portions 71c of the contact fittings 71 held by the second housing 51b face and are in contact with the respective back-surface electrodes 21b of the sensor element 20 (see FIG. 4 and FIG. 5). Each upright portion 71d has a hook 71e having a curved shape and retained by the retainer 54.

The positional relationship between the contact fittings 71 and the electrodes 21 of the sensor element 20 will now be described. As illustrated in FIG. 4 and FIG. 6, the front-surface electrodes 21a of the sensor element 20 extend from the base end of the sensor element 20 to a position between the conducting portions 71c and the supporting portions 71b. Of the four front-surface electrodes 21a arranged in the Y direction, two front-surface electrodes 21a in the middle are electrically connected to respective through holes 21e formed for electrical connection to the electric paths inside the sensor element 20. As illustrated in FIG. 6, each of the through holes 21e is at a position between the conducting portion 71c and the supporting portion 71b. Note that the positional relationship between the back-surface electrodes 21b and the contact fittings 71, and the positions of through holes 21e electrically connected to the back-surface electrodes 21b are the same as this, and thus will not be described here.

The clamp 90 is formed by bending a metal plate. The clamp 90 has an elastic force that can clamp the first housing 51a and the second housing 51b and press them closer to each other. When the first housing 51a and the second housing 51b are clamped by the elastic force, the regulating members 56 and 57 of the first housing 51a come into contact with the second housing 51b, while the regulating members 56 and 57 of the second housing 51b come into contact with the first housing 51a. Thus, the distance between the first housing 51a and the second housing 51b is fixed. When the clamp 90 clamps the first housing 51a and the second housing 51b, with the sensor element 20 sandwiched between the first housing 51a and the second housing 51b, such that the conducting portions 71c of the contact fittings 71 face the front-surface electrodes 21a or the back-surface electrodes 21b of the sensor element 20, the pressing force of the clamp 90 elastically deforms the supporting portions 71b and the conducting portions 71c, which then clamp and secure the sensor element 20. Since the supporting portions 71b and the conducting portions 71c are elastically deformed, the sensor element 20 can be reliably clamped and secured by the resulting pressing force. Since the conducting portions 71c are elastically deformed, the electrical contact between the conducting portions 71c and the electrodes 21 can be reliably maintained.

Moreover, since the distance between the first housing 51a and the second housing 51b is fixed by the regulating members 56 and 57, even if excessive pressure is externally applied, the supporting portions 71b and the conducting portions 71c are not affected by the pressure and can be prevented from being plastically deformed. It is thus possible to maintain the electrical contact between the connector 50 and the sensor element 20 and the clamping of the sensor element 20 for a long period of time.

Figure 7:
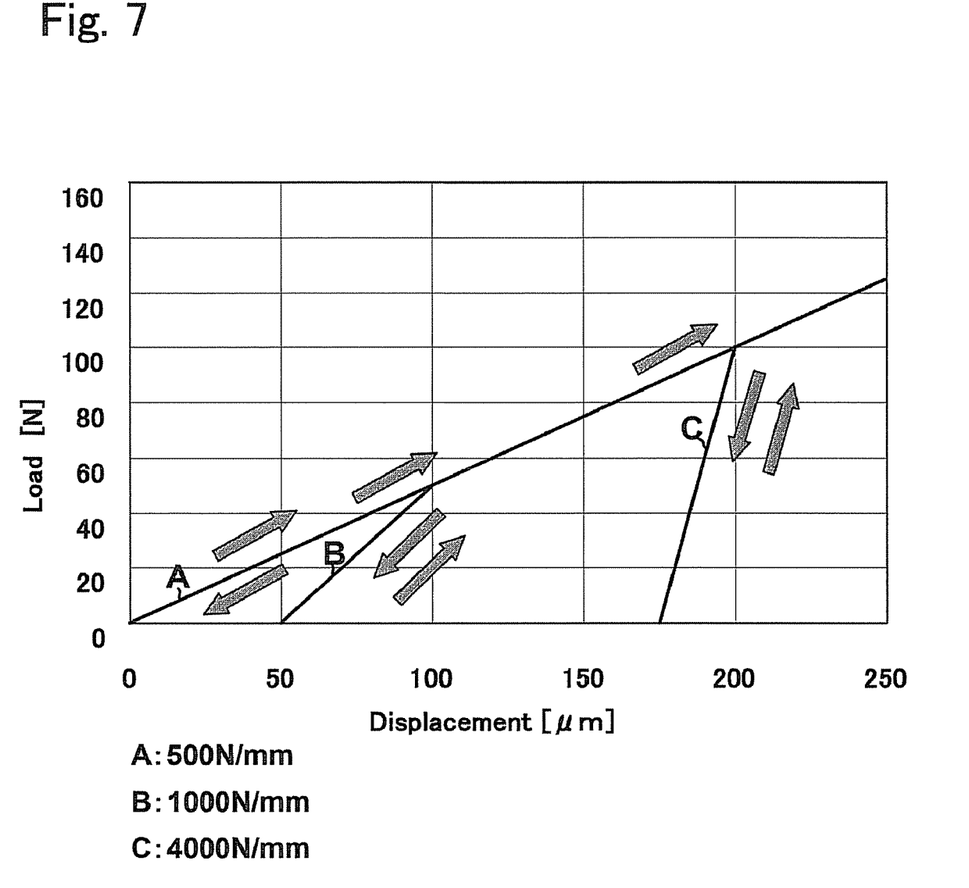
FIG. 7 is a graph showing a relationship between load and displacement of supporting portions 71b and conducting portions 71c.

The material of the supporting portions 71b and the conducting portions 71c and how the supporting portions 71b and the conducting portions 71c are to be bent are determined such that the supporting portions 71b and the conducting portions 71c are not plastically deformed at, or within a predetermined margin of, the pressing force of the clamp 90 in a state where the distance between the first housing 51a and the second housing 51b is fixed by the regulating members 56 and 57. The spring constant of each of the supporting portion 71b and the conducting portion 71c is preferably in the range of 500 N/mm to 4000 N/mm. This spring constant is a spring constant in a direction (Z direction) orthogonal to a line tangent to the tip of each of the supporting portion 71b and the conducting portion 71c assembled to each housing 51. With this spring constant, the above-described effects can be more reliably achieved. For example, since the supporting portions 71b and the conducting portions 71c are not subjected to any load and not displaced immediately after production of the contact fittings 71, both displacement and load are zero (corresponding to the origin of the graph) as illustrated in FIG. 7. On the other hand, when the sensor element 20 is assembled to the connector 50, the supporting portions 71b and the conducting portions 71c are subjected to load and compressed in the Z direction. Therefore, the displacement increases as the load increases. The displacement changes along a straight line A (corresponding to a spring constant of 500 N/mm) in FIG. 7. After assembly of the sensor element 20 to the connector 50, the load is 50 N and the displacement is 100 μm. Then, if the load decreases in the range of 0 N to 50 N, the displacement decreases as indicated by a downward arrow along the straight line A, whereas if the load increases, the displacement increases as indicated by an upward arrow along the straight line A. By appropriately determining the material of the supporting portions 71b and the conducting portions 71c and how the supporting portions 71b and the conducting portions 71c are to be bent, it is possible to realize the initial relationship between load and displacement indicated by the straight line A, and the relationship between load and displacement after the assembly also indicated by the straight line A. The material etc. may be determined such that, after the sensor element 20 is assembled to the connector 50 and the load and the displacement reach 50 N and 100 μm, respectably, if the load decreases in the range of 0 N to 50 N, the displacement decreases as indicated by a downward arrow along a straight line B (corresponding to a spring constant of 1000 N/mm), whereas if the load increases, the displacement increases as indicated by an upward arrow along the straight line B. Alternatively, the material etc. may be determined such that, after the sensor element 20 is assembled to the connector 50 and the load and the displacement reach 100 N and 200 μm, respectably, if the load decreases in the range of 0 N to 100 N, the displacement decreases as indicated by a downward arrow along a straight line C (corresponding to a spring constant of 4000 N/mm), whereas if the load increases, the displacement increases as indicated by an upward arrow along the straight line C. Thus, as described above, the spring constant of each of the supporting portion 71b and the conducting portion 71c after assembly of the sensor element 20 to the connector 50 can be set to be in the range of 500 N/mm to 4000 N/mm.

In the contact fittings 201a to 201c of the related art illustrated in FIG. 10, the protrusions 202a to 202c are in contact with the electrodes. Unlike the supporting portions 71b and the conducting portions 71c of the present embodiment formed by bending a metal plate, the protrusions 202a to 202c do not have an elastic force. Therefore, when the sensor element is clamped by the two housings 200, if there is a member, such as the regulating members 56 and 57 of the present embodiment, that fixes the distance between the housings, the protrusions 202a to 202c may float from the electrodes and an adverse effect may occur depending on the accuracy of the member. Even if there is no member that fixes the distance between the housings, since the protrusions are not elastically deformed, the protrusions may float from the electrodes depending on the accuracy of other members. This may be less likely to occur in the example of FIG. 10 where there are three protrusions, as there is always a plane that is tangent to all the three points. However, such a problem is likely to occur if four or more protrusions are necessary.

Figure 8:
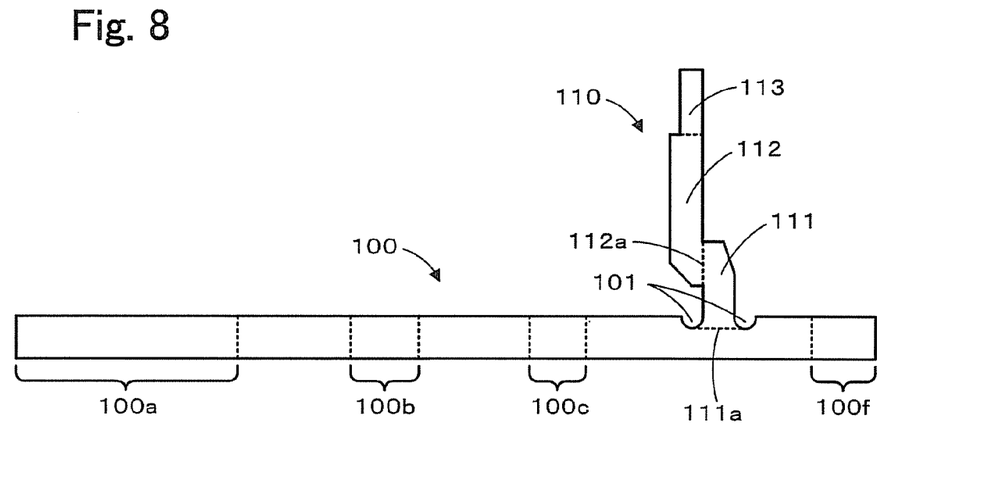
FIG. 8 illustrates a contact fitting 71 before being bent.
Figure 9:
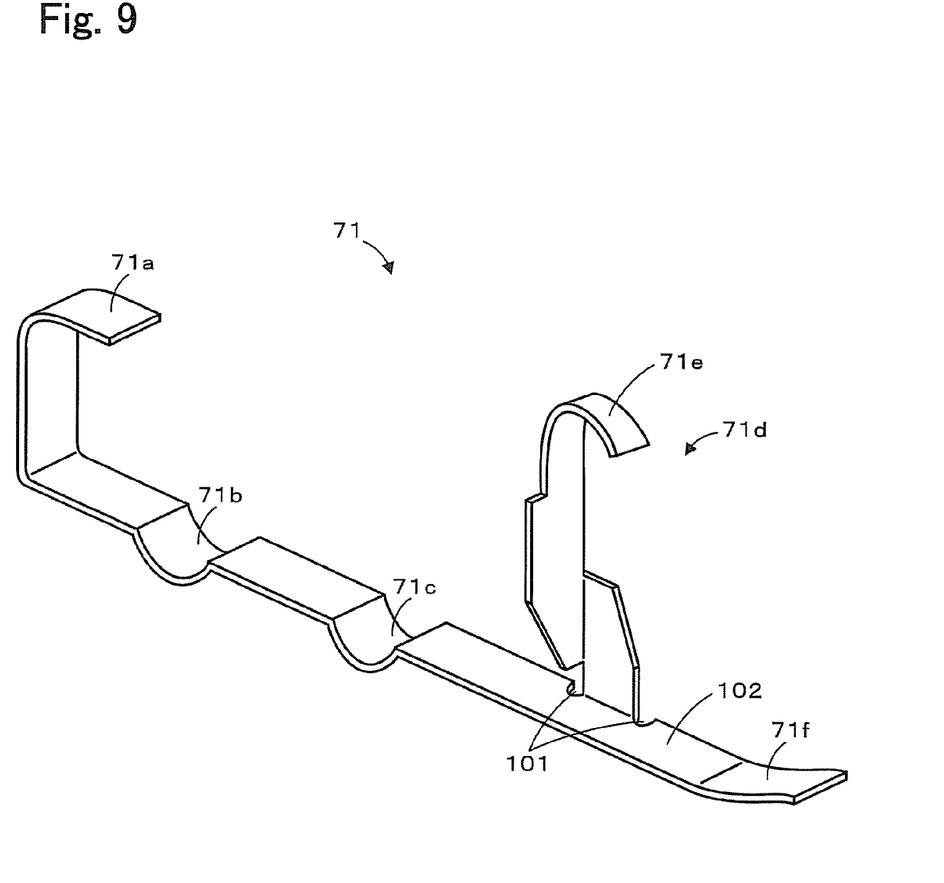
FIG. 9 illustrates a bent contact fitting 71.

A method for making the contact fittings 71 will now be described. Each of the contact fittings 71 is formed by die-cutting and bending a metal plate. First, as illustrated in FIG. 8, a metal plate is die-cut into a shape shaving a metal plate portion 100 of substantially rectangular shape and a metal piece 110 connecting to a long side of the metal plate portion 100. Next, the tip portion 71a and the connecting portion 71f illustrated in FIG. 4 are formed by bending a region 100a and a region 100f, respectively, of the metal plate portion 100 upward from the horizontal plane of FIG. 8. Also, the supporting portion 71b and the conducting portion 71c illustrated in FIG. 4 are formed by bending a region 100b and a region 100c, respectively, of the metal plate portion 100 downward from the horizontal plane of FIG. 8. The hook 71e is formed by folding a region 111 along a straight line 111a upward 90° from the horizontal the plane of FIG. 8, folding a region 112 along a straight line 112a toward the inside of the metal plate portion 100, and bending a region 113 along the length of the metal plate portion 100 toward the connecting portion 71f. Thus, the metal piece 110 is bent to form the upright portion 71d. The contact fitting 71 formed by bending is illustrated in FIG. 10. In the process described above, the contact fitting 71 of three-dimensional shape can be easily made from a metal sheet. As illustrated in FIG. 8 and FIG. 9, the metal plate portion 100 is provided with cutouts 101 having a depth greater than or equal to the thickness of the region 111. Thus, when the region 111 is folded along the straight line 111a, the region 111 can be accommodated within a region directly above a front surface 102 of the metal plate portion 100. The widths of the regions 112 and 113 are determined such that the regions 112 and 113 can also be accommodated within the region directly above the front surface 102 of the metal plate portion 100. Since the hook 71e is formed by bending the region 113 along the length of the metal plate portion 100 toward the connecting portion 71f, the entire upright portion 71d is also accommodated within the region directly above the front surface 102 of the metal plate portion 100. When the upright portions 71d of the plurality of contact fittings 71 are formed into the above-described shape, it is possible to reduce the arrangement width of the contact fittings 71 arranged in a direction orthogonal to the length of the contact fittings 71, and thus to reduce the size of the housings 51. This means that the size of the connector 50 can be reduced. Moreover, since the connector 50 and the sensor element 20 communicate with each other through the contact fittings 71 which are elastic bodies, vibration transmitted from the outer cylinder 46, through the rubber stopper 47, to the lead wires 45, and to the connector 50 is not directly transmitted to the sensor element 20. In the related art such as that illustrated in FIG. 10, the connector 50 and the sensor element 20 communicate with each other through the non-elastic protrusions 202a to 202c of the contact fittings 201a to 201c. Therefore, vibration transmitted from the outer cylinder 46, through the rubber stopper 47, to the lead wires 45, and to the connector 50 is directly transmitted to the sensor element 20. Moreover, if the gas sensor 10 is installed in a vibrating environment such as in a vehicle, the sensor element 20 and the connector 50 vibrate, as described above, with respect to the upper end portion P illustrated in FIG. 1. In such a case, if the contact fittings 71 do not have an elastic force, the lead wires 45, the rubber stopper 47, and the outer cylinder 46, as well as the connector 50, are included in the vibrating system of the sensor element 20. This raises a concern about the occurrence of excessive repeated stress with respect to the upper end portion P described above. However, such a concern can be effectively resolved in the present embodiment, where the contact fittings 71 being elastic bodies allow communication between the connector 50 and the sensor element 20. Additionally, since moment generated in the connector 50 by vibration can be reduced as the size or weight of the connector 50 decreases, the repeated stress on the sensor element 20 caused by moment of the connector 50 can be reduced. Thus, the life of the sensor element 20 can be extended. Moreover, since moment generated in the connector 50 can be reduced, it is possible to make the connector 50 more resistant to vibration and extend the life of the connector 50. In the contact fittings 201a to 201c of the related art illustrated in FIG. 10, the hooks 203a to 203c are orthogonal to the length of the contact fittings 201a to 201c and bend outward from the contact fittings 201a to 201c. As a result, since it is necessary to increase the width of arrangement of the contact fittings 201a to 201c by the size of the hooks 203a to 203c, the size of the housing 200 is increased. As illustrated in FIG. 10, to minimize the size of the housing 200, the width of arrangement of the contact fittings 201a to 201c is increased only in an area around the hooks 203a to 203c and is reduced in an area around the protrusions 202a to 202c. However, as illustrated in FIG. 10, since the contact fittings 201a to 201c have different shapes, it is necessary to produce the contact fittings 201a to 201c in different processes. In the present embodiment, in contrast, it is possible to realize the plurality of contact fittings 71 having the same shape, and provide the connector 50 smaller in size than that of the related art.

In the embodiments described above in detail, each of the contact fittings 71 is obtained by bending a die-cut member having the metal plate portion 100 of substantially rectangular shape and the metal piece 110 connecting to a long side of the metal plate portion 100. The metal piece 110 is folded to be accommodated within a region directly above a surface of the metal plate portion 100 opposite a surface in contact with the front-surface electrode 21a or the back-surface electrode 21b. Then, the metal piece 110 is bent along the length of the metal plate portion 100 to form the hook 71e to be retained by the first housing 51a or the second housing 51b. Therefore, as compared to the structure in which the hooks are orthogonal to the length of the metal plate portions and bend outward from the contact fittings, the arrangement width of the contact fittings 71 arranged in a direction substantially orthogonal to the length of the contact fittings 71 can be reduced, so that the size of the first housing 51a and the second housing 51b can be reduced. This means that it is possible to reduce the size of the connector 50.

The clamp 90 applies pressure to bring the first housing 51a and the second housing 51b closer to each other, with the front-surface electrodes 21a and the back-surface electrodes 21b facing the conducting portions 71c. Thus, the distance between the first housing 51a and the second housing 51b can be fixed by the regulating members 56 and 57. At the same time, the sensor element 20 is clamped and secured by pressing force generated by elastic deformation of the conducting portions 71c. Thus, since the conducting portions 71c are less likely to separate from the sensor element 20, it is possible to reliably maintain the electrical contact between the conducting portions 71c and the front-surface electrodes 21a and between the conducting portions 71c and the back-surface electrodes 21b, and to reliably clamp the sensor element 20. Additionally, since the distance between the first housing 51a and the second housing 51b is fixed by the regulating members 56 and 57, even if excessive pressure is externally applied, the conducting portions 71c are not affected by the pressure and can be prevented from being plastically deformed. It is thus possible to maintain the electrical contact and the clamping of the sensor element 20 for a long period of time, and to ensure longer life of the connector 50. The above-described effects can be more reliably achieved when the spring constant of the conducting portions 71c is in the range of 500 N/mm to 4000 N/mm.

It is to be understood that the present invention is not limited to the embodiments described above, and can be realized in various forms within the technical scope of the present invention.

For example, although the first housing 51a and the second housing 51b each have the regulating members 56 and 57 in the embodiments described above, the regulating members 56 and 57 may be separate from the first housing 51a and the second housing 51b. Alternatively, each of the first housing 51a and the second housing 51b may have regulating members in both sides thereof, so that the distance between the first housing 51a and the second housing 51b is fixed by contact between their opposite regulating members.

Although both the supporting portions 71b and the conducting portions 71c are configured to clamp the sensor element 20 with pressing force in the embodiments described above, the supporting portions 71b may not be provided. However, as described above, if the conducting portions 71c are located on a side of the through holes 21e adjacent to the base end of the sensor element 20, the pressing force from the conducting portions 71c may act on the through holes 21e and cause cracks in the sensor element 20. To prevent this, it is preferable that the sensor element 20 be clamped also by the supporting portions 71b.

Although the hooks 71e bend toward the connecting portions 71f in the embodiments described above, they may bend in the opposite direction. In the latter case, the retainer 54 in each insertion hole 53 may be formed on the opposite side in the insertion hole 53. The upright portions 71d of the contact fittings 71 may be formed by any folding and bending process, as long as each of the upright portions 71d is accommodated within a region directly above the front surface 102 of the metal plate portion 100.

The present application claims priority from Japanese Patent Application No. 2009-295652 filed on Dec. 25, 2009, the entire contents of which are incorporated in the present specification by reference.

INDUSTRIAL APPLICABILITY

The connector of the present invention is electrically connected to a plurality of front-surface electrodes arranged side by side on a front surface of a planar sensor element and to a plurality of back-surface electrodes arranged side by side on a back surface of the sensor element. For example, the connector of the present invention can be used in a gas sensor, such as an $O_2$ sensor, a NOx sensor, or an ammonia gas sensor.

The invention claimed is:

1. A connector electrically connected to a plurality of front-surface electrodes arranged side by side on a front surface of a planar sensor element and to a plurality of back-surface electrodes arranged side by side on a back surface of the sensor element, the connector comprising:
   a first housing configured to hold a plurality of long narrow contact fittings arranged at respective positions opposite the plurality of front-surface electrodes of the sensor element in a direction substantially orthogonal to the length of the contact fittings; and
   a second housing configured to hold a plurality of long narrow contact fittings arranged at respective positions opposite the plurality of back-surface electrodes of the sensor element in a direction substantially orthogonal to the length of the contact fittings,
   wherein each of the contact fittings is obtained by bending a die-cut member having a metal plate portion of substantially rectangular shape and a metal piece connecting to a long side of the metal plate portion; the metal plate portion has a conducting portion that can be in contact with the front-surface electrode or the back-surface electrode; and the metal piece is folded to be accommodated within a region directly above a surface of the metal plate portion opposite a surface in contact with the front-surface electrode or the back-surface electrode, and bent along the length of the metal plate portion to foam a hook to be retained by the first housing or the second housing.

2. The connector according to claim 1, wherein the metal plate portion of each of the contact fittings has a supporting portion that can be in contact with a portion of the front surface of the sensor element where the front-surface electrode is not present, or with a portion of the back surface of the sensor element where the back-surface electrode is not present.

3. The connector according to claim 2, further comprising:
   regulating members configured to regulate a distance between the first housing and the second housing; and
   a housing securing member configured to apply pressure to bring the first housing and the second housing closer to each other, with the front-surface electrodes of the sensor element facing the respective conducting portions of the contact fittings on the first housing, the portion of the front surface of the sensor element where the front-surface electrodes are not present facing the supporting portions of the contact fittings on the first housing, the back-surface electrodes of the sensor element facing the respective conducting portions of the contact fittings on the second housing, and the portion of the back surface of the sensor element where the back-surface electrodes are not present facing the supporting portions of the contact fittings on the second housing, allow the regulating members to fix the distance between the first housing and the second housing, and clamp and secure the sensor element with pressing force generated by elastic deformation of the conducting portions and the supporting portions of the contact fittings on the first housing and the conducting portions and the supporting portions of the contact fittings on the second housing.

4. The connector according to claim 3, wherein a spring constant of the conducting portion of each of the contact fittings is in the range of 500 N/mm to 4000 N/mm.

5. The connector according to claim 1, further comprising:
regulating members configured to regulate a distance between the first housing and the second housing; and
a housing securing member configured to apply pressure to bring the first housing and the second housing closer to each other, with the front-surface electrodes of the sensor element facing the respective conducting portions of the contact fittings on the first housing and the back-surface electrodes of the sensor element facing the respective conducting portions of the contact fittings on the second housing, allow the regulating members to fix the distance between the first housing and the second housing, and clamp and secure the sensor element with pressing force generated by elastic deformation of the conducting portions of the contact fittings on the first housing and the conducting portions of the contact fittings on the second housing.

6. The connector according to claim 5, wherein a spring constant of the conducting portion of each of the contact fittings is in the range of 500 N/mm to 4000 N/mm.

* * * * *

UNITED STATES PATENT AND TRADEMARK OFFICE
CERTIFICATE OF CORRECTION

PATENT NO.       : 8,287,294 B2
APPLICATION NO.  : 13/194088
DATED            : October 16, 2012
INVENTOR(S)      : Koichi Masuda, Hirohito Kiyota and Nobukazu Ikoma It is certified that error appears in the above-identified patent and that said Letters Patent is hereby corrected as shown below:

Column 10, Line 34

(claim), line 27: please change "foam" to --form--.

Signed and Sealed this
Fourth Day of December, 2012

David J. Kappos
*Director of the United States Patent and Trademark Office*

UNITED STATES PATENT AND TRADEMARK OFFICE
CERTIFICATE OF CORRECTION

PATENT NO. : 8,287,294 B2
APPLICATION NO. : 13/194088
DATED : October 16, 2012
INVENTOR(S) : Koichi Masuda, Hirohito Kiyota and Nobukazu Ikoma Page 1 of 1

It is certified that error appears in the above-identified patent and that said Letters Patent is hereby corrected as shown below:

Column 10, Line 34

(Claim 1, line 27) please change "foam" to --form--.

This certificate supersedes the Certificate of Correction issued December 4, 2012.

Signed and Sealed this
Nineteenth Day of February, 2013

Teresa Stanek Rea
*Acting Director of the United States Patent and Trademark Office*